United States Patent [19]
Ito

[11] Patent Number: 6,042,377
[45] Date of Patent: Mar. 28, 2000

[54] DENTAL HANDPIECE WITH DETACHABLE MOTOR

[75] Inventor: Yukio Ito, Kanuma, Japan

[73] Assignee: Nakanishi, Inc., Tokyo, Japan

[21] Appl. No.: 09/158,226

[22] Filed: Sep. 22, 1998

[30] Foreign Application Priority Data

Sep. 24, 1997 [JP] Japan .................................. 9-258426

[51] Int. Cl.[7] .................. A61C 1/08; A61C 1/00
[52] U.S. Cl. ............................ 433/126; 433/131
[58] Field of Search ............... 433/29, 114, 126, 433/131

[56] References Cited

U.S. PATENT DOCUMENTS

| | | | |
|---|---|---|---|
| 4,669,982 | 6/1987 | Fleer | 433/126 |
| 4,983,121 | 1/1991 | Straihammer et al. | 433/126 X |
| 5,599,143 | 2/1997 | Dusing | 433/126 X |
| 5,609,445 | 3/1997 | Dusing | 433/126 X |
| 5,741,084 | 4/1998 | Del Rio et al. | 433/126 X |

*Primary Examiner*—Nicholas D. Lucchesi
*Attorney, Agent, or Firm*—Malcolm B. Wittenberg; Crosby, Heafey, Roach & May

[57] ABSTRACT

A dental handpiece having a detachable motor. The dental handpiece includes a handpiece body having a dental tool, a driving section detachably connected to the handpiece body, the driving section further including a motor for operatively driving the dental tool, and a motor casing having a substantially tubular wall for defining a motor cavity for accommodating the motor. The motor casing allows the motor to be inserted and removed in an axial direction including a fastener for holding the motor in position in the motor casing.

14 Claims, 3 Drawing Sheets

DENTAL HANDPIECE WITH DETACHABLE MOTOR

BACKGROUND OF THE INVENTION

The present invention relates to a dental handpiece, in particular, a dental handpiece of a motor driven type which can be sterilized conveniently.

Tools and instruments used for dental treatment are sterilized after use for each patient in order to prevent cross infection between patients. Such sterilization is usually performed with, for example, boiling water, high-pressure steam (autoclaving or chemi-claving), EOG (ethylene oxide gas), ultraviolet, or alcohol. Among them, sterilization of dental handpieces is mainly carried out with high-pressure steam or EOG.

Sterilization of motor-driven dental handpieces by the above-mentioned way often causes deterioration of brushes in the motor due to the steam intrusion. Further, since such sterilization is carried out at an elevated temperature, sensors in brushless motors tend to be damaged by heat. Therefore, it is desirable to take the motor away from the handpiece before sterilization of the handpiece.

However, the motor is integrally and undetachably built in the handpiece driving section. Thus, it is hard to remove only the motor from the handpiece, nor is it practical to do this after use for each patient.

Accordingly, with a handpiece which can be divided into a handpiece body and a driving section, only the handpiece body is conventionally subjected to the sterilization such as autoclaving, while the driving section accommodating the motor is merely wiped with alcohol.

This driving section accommodates a variety of fluid passages, and is exposed to direct contact with users such as dentists. Therefore, it is desirable to sterilize the driving section sufficiently by autoclaving and the like method.

SUMMARY OF THE INVENTION

Therefore, it is an object of the present invention to provide a dental handpiece in which the motor is detachably mounted.

It is another object of the present invention to provide a dental handpiece of which driving section, independently from the motor, can be subjected to sterilization such as autoclaving.

According to the present invention, there is provided a dental handpiece comprising:

a handpiece body having a dental tool, a driving section detachably connected to the handpiece body, said driving section further comprising a motor for operatively driving the dental tool, and a motor casing having a substantially tubular wall for defining a motor cavity for accommodating said motor, said motor casing allowing the motor to be inserted and removed in an axial direction, and fastening means for holding the motor in position in the motor casing.

With the present dental handpiece, the motor can easily be detached from the motor casing by removing the fastening means from the motor casing, and can be mounted and held in place in the motor casing by attaching fastening means to the motor casing. Accordingly, the motor can be removed from the driving section easily to enable sterilization of the driving section without the motor by a desired process such as autoclaving.

According to the present invention, the motor casing may be of cylindrical or prismatic shape. The motor may be inserted into the motor casing through the proximal or distal end of the motor casing.

When the motor is to be inserted into the motor casing through the distal end of the casing, the handpiece body may be made to function as the fastening means.

The fastening means prevents excess axial displacement of the motor in the motor casing to hold the motor in the optimal position for transmitting driving force to the handpiece body.

PREFERRED EMBODIMENT OF THE INVENTION

Preferred embodiments of the present invention will be explained with reference to the attached drawings.

Figure 1:
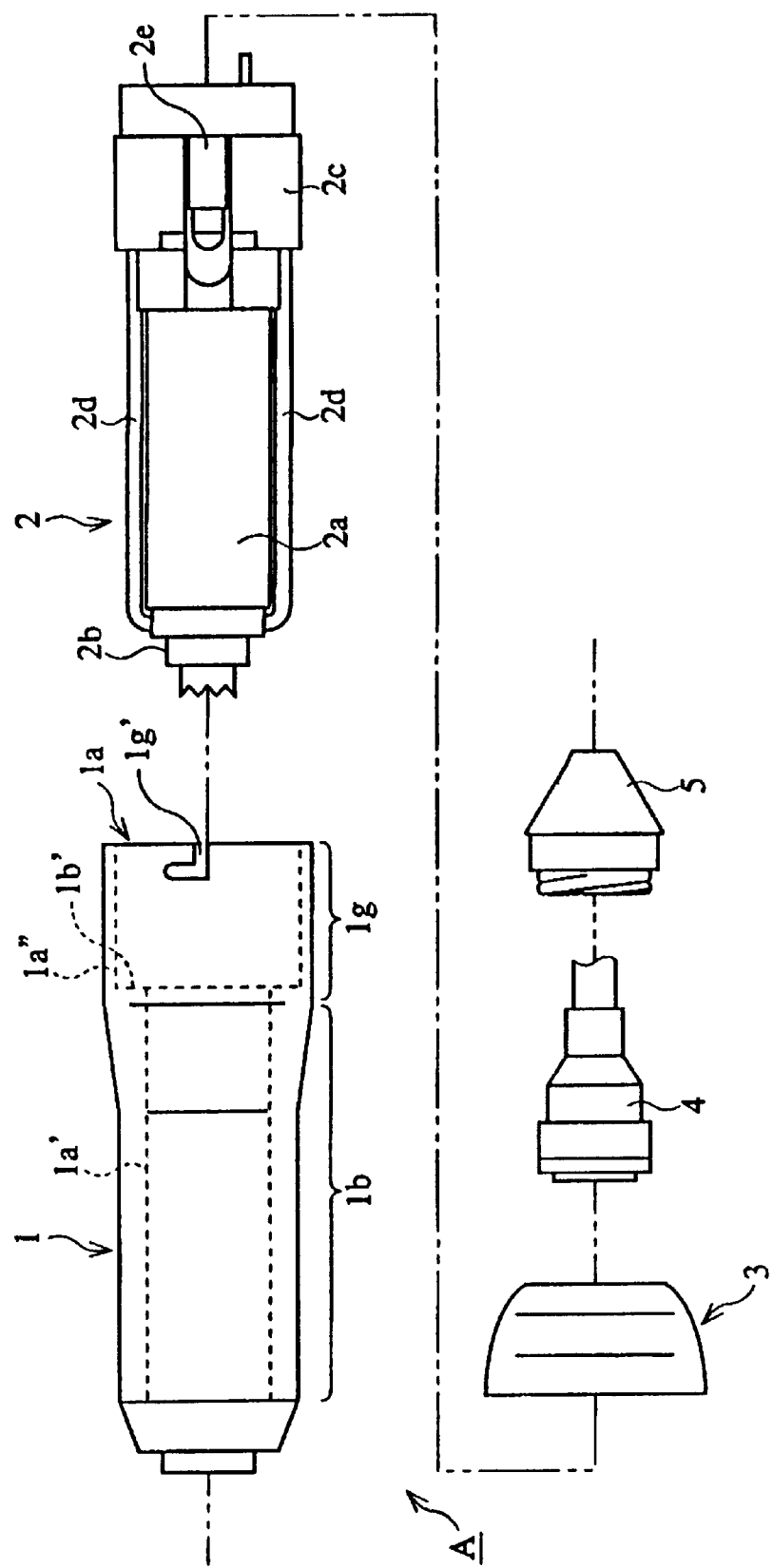
FIG. 1 is an exploded view of an embodiment of a driving section A of a dental handpiece according to the present invention.

FIG. 1 is an exploded view of a driving section A of a dental handpiece according to the present invention. The driving section A is detachably connected to a handpiece body (not shown) at its distal end in a conventional fashion, so that the connection between the two is not described in detail. The driving section A includes motor casing 1, motor assembly 2 detachably accommodated in the casing 1, and annular cap 3 (fastening means) detachably attached to the proximal end of the casing 1.

The motor casing 1 has a generally cylindrical shape with a motor cavity 1a extending therethrough. The motor cavity 1a has two portions; smaller diameter portion 1a' defined by thickened wall portion 1b of the casing 1, and larger diameter portion 1a" defined by thinned wall portion 1g of the casing 1. As can be best seen from FIG. 4, the central axis of the smaller diameter portion 1a' is displaced with respect to the central axis of the motor casing 1. In this embodiment, the motor assembly 2 is inserted into the motor cavity in the casing 1 through the proximal end of the casing 1.

Figure 3:
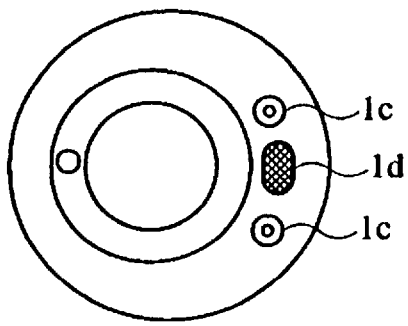
FIG. 3 is a distal end view of motor casing 1 of the driving section A shown in FIG. 1.
Figure 4:
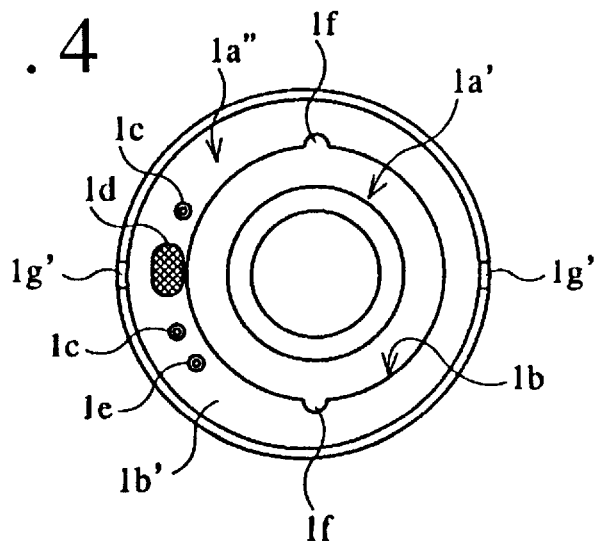
FIG. 4 is a proximal end view of the motor casing 1.

As shown in FIG. 4, which is a proximal end view of the casing 1, the thickened wall portion 1b is provided with two diametrally opposing grooves 1f on the inner surface thereof extending in the axial direction of the casing 1. In the thickened wall portion 1b of the casing 1, there are axially extending in parallel two fluid passages 1c for supplying water and chip air and an optical fiber cable 1d. Also extending axially in the portion 1b is motor-cooling air passage 1e from the proximal end face 1b' midway through the portion 1b. The fluid passages 1c and the optical fiber cable 1d are connected to the corresponding passages and cable extending in the handpiece body (not shown) when the driving section is connected to the handpiece body for transmission of water, chip air, and light. In this embodiment, as shown in FIGS. 3 and 4, the cross section of the optical fiber cable has elliptical shape for effective use of the installation space with sufficient light amount.

The thinned wall portion 1g defining the larger diameter portion 1a" of the motor cavity 1a has two diametrally opposing notches 1g' at its proximal end. Each notch extends for a length from the proximal end of the thinned wall portion 1g and then bent at right angle to extend for a length in the circumferential direction of the casing 1. The circumferentially extending portions of the two notches are oriented in the same circumferential direction.

Figure 5:
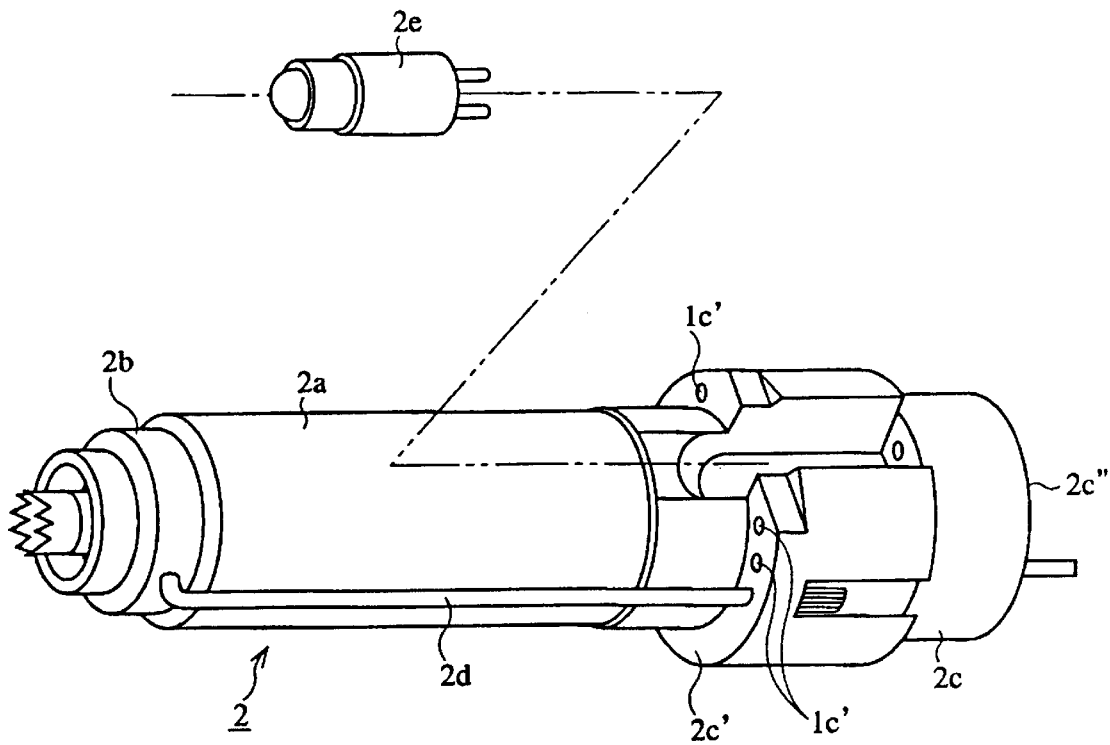
FIG. 5 is a perspective view of motor assembly 2 of the driving section A.

As shown in FIG. 5, the motor assembly 2 includes motor body 2a having a gear on the distal end of its output axis, motor cap 2b mounted on the distal end of the motor body 2a, motor connector 2c mounted on the proximal end of the motor body 2a, and anti-rotation bars 2d disposed along the motor body 2a.

The central axis of the motor body 2a is displaced from the central axis of the motor connector 2c corresponding to the displacement of the smaller diameter portion 1a' of the motor cavity 1a with respect to the motor casing 1.

The motor connector 2c has distal and proximal end faces 2c' and 2c" and three fluid passages 1c' extending between these faces. On the connector 2c is also mounted a bulb 2e for providing light to the optical fiber cable 1d. When the driving section A is assembled by inserting the motor assembly 2 into the casing 1, the distal end face 2c' abuts the proximal end face 1b' of the thickened wall portion 1b. As a result, the fluid passages 1c' in the connector 2c are connected to the fluid passages 1c in the casing 1, and the bulb 2e is positioned in alignment with the proximal end face of the optical fiber cable 1d. The proximal end face 2" of the connector 2c is connected to cable connector 4 to supply the fluids through the fluid passages 1c' to the fluid passages 1c. The bulb 2e and the motor body 2a are fed through the cable connector 4 via wires (not shown) extending through the connector 2c.

The anti-rotation bar 2d is attached by fitting the distal end thereof in a hole in the outer surface of the motor cap 2b, and securing the proximal end thereof to the motor connector 2c with a screw. Two of anti-rotation bars 2d are positioned along the motor body 2a at diametrally opposite location corresponding to the location of the grooves if on the thickened wall portion 1b of the casing 1. Accordingly, when the motor assembly 2 is inserted into the casing 1, the bars 2d are detachably received and fit in the grooves if to prevent the motor assembly 2 from rotating in the casing 1. Also, the cooperation of the anti-rotation bars 2d and the grooves if, along with the displaced smaller diameter portion 1a' of the motor cavity 1a, facilitates circumferential alignment of the motor assembly 2 with respect to the motor cavity 1a.

Figure 6:
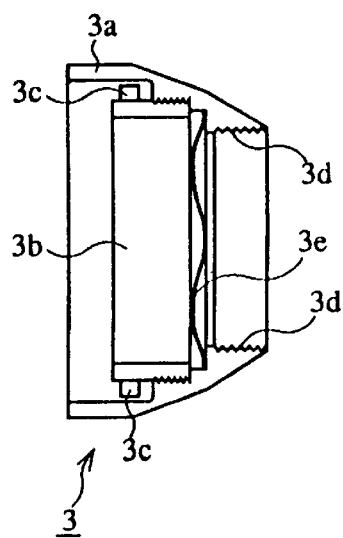
FIG. 6 is a longitudinal sectional view of annular cap 3.

As shown in FIG. 6 in section, the annular cap 3 is composed of outer ring 3a and inner ring 3b which is screwed and adhered on the inner surface of the outer ring 3a. The inner surface of the outer ring 3a is threaded in the proximal portion 3d so that connector ring 5 may be screwed thereto. The inner ring 3b has two projections 3c on its outer surface at diametrally opposite position for engaging in the corresponding notches 1g' on the casing 1.

Wave washer 3e is disposed in the outer ring 3a adjacent to the proximal end face of the inner ring 3b. In FIG. 6, only the washer 3e is shown in side view. When the driving section A is assembled, proximal portion of the motor connector 2c is received in the inner ring 3b with the wave washer 3e abutting the proximal end face 2c" for urging the motor assembly 2 distally.

Next, assembly of the driving section A is discussed.

First, the motor assembly 2 is inserted into the motor cavity 1a in the motor casing 1 through the proximal end of the casing 1, with the anti-rotation bars 2d on the assembly 2 being received and advancing in the grooves 1f. The insertion is completed when the distal end face 2c' of the connector 2c abuts the proximal end face 1b' of the thickened wall portion 1b. In this position, the fluid passages 1c' in the connector 2c are connected to the fluid passages 1c in the casing 1, and the bulb 2e on the connector 2c is disposed adjacent to the proximal end face of the optical fiber cable 1d in the casing 1.

Due to the displacement of the central axis of the smaller diameter portion 1a' with respect to the central axis of the motor casing 1, the motor assembly 2 will not be circumferentially misaligned to the casing 1. Even if the motor assembly 2 is inserted with wrong circumferential alignment to the casing 1, the connector 2c will be caught on the way, and cannot be advanced through the motor cavity 1a to the position where the distal end face 2c' of the connector 2c abuts the proximal end face 1b' of the thickened wall portion 1b. Therefore, accidental contact of the motor connector 2c with the fluid passages 1c projecting from the proximal end face 1b' may be avoided to prevent the passages 1c from being damaged.

When the motor assembly 2 is fully inserted and arranged in position in the motor casing 1, annular cap 3 is attached to the proximal end of the casing 1 to secure the assembly 2 in position in the casing 1. Specifically, the annular cap 3 is first pressed in the axial direction to insert the projections 3c axially into the notches 1g' on the casing 1, and then rotated in the direction of the circumferentially bent portion of the notches 1g' to position the projections 3c in the bent portion of the notches 1g', thereby fixing the annular cap 3 on the casing 1. In this position, the wave washer 3e constantly presses the proximal end face 2c" of the connector 2c distally, so that the motor assembly 2 is held in place in the casing 1 without excess axial displacement. Yet, the motor assembly 2 has some axial play in the casing 1 due to the elastic deformation of the wave washer 3e, which facilitates smooth meshing of the gears upon connection of the driving section A to the handpiece body (not shown).

Finally, the cable connector 4 is inserted through the proximal end of the annular cap 3 to connect the connector 4 to the proximal end face 2c" of the motor connector 2c. Then the connector ring 5 is screwed onto the proximal end of the annular cap 3 to ensure the connection between the cable connector 4 and the motor connector 2c.

Alternatively, the connector ring 5 may be made to be screwed onto the proximal end of the connector 2c, rather than onto the proximal end of the annular cap 3. With this structure, the motor assembly 2 with cables may be easily detached from the motor casing 1 simply by holding and pulling the annular cap 3 or connector ring 5.

Figure 2:
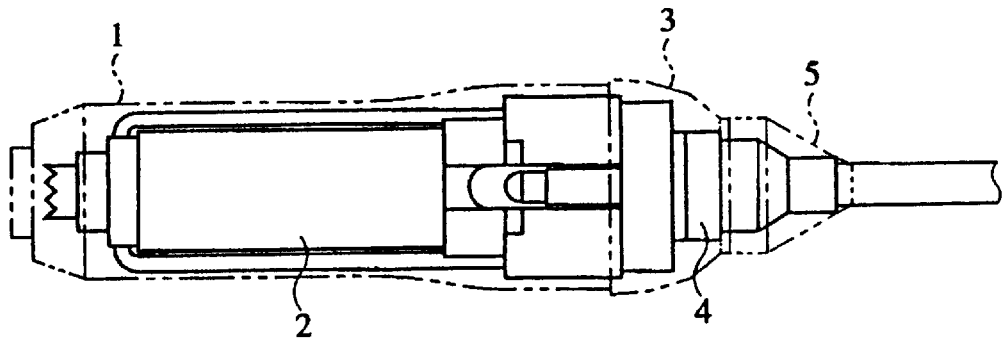
FIG. 2 illustrates the driving section A of FIG. 1 in an assembled state.

FIG. 2 shows the driving section A thus assembled. Before use in dental treatment, a handpiece body (not shown) is connected to the distal end of the driving section A. Disassembly of the driving section A may be carried out following the above-mentioned process in the reverse order.

It is the motor casing 1 that particularly needs to be sterilized after use. According to the present invention, the motor casing 1 may be detached simply by rotating the casing 1 with respect to the annular cap 3 to release the engagement of the projections 3c in the notches 1g', and pulling the casing 1 distally. This easy detachment enables and facilitates sterilization of the casing 1 after use for each patient.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece including, a handpiece section having a dental tool, and a driving section detachably connected to the handpiece section, said driving section comprising:

a motor casing having a substantially tubular wall for defining a motor cavity therein, and a motor slidably received within said motor cavity and being slidably removable therefrom in an axial direction, and a cap detachably coupled to a proximal end of said motor casing for releasably holding said motor in position in said motor cavity.

2. The dental handpiece of claim 1 wherein said substantially tubular wall of the motor casing has an inner surface, wherein said driving section further comprises two anti-rotation bars extending axially along and attached to said motor, said inner surface of said tubular wall having two axially extending grooves at diametrally opposite location for receiving said two anti-rotation bars.

3. The dental handpiece of claim 2 wherein said motor cavity has a larger diameter portion and a smaller diameter portion, said smaller diameter portion having a central axis displaced with respect to a central axis of said motor casing.

4. The dental handpiece of claim 3 wherein said driving section further comprises a motor connector, said motor connector having a central axis displaced with respect to a central axis of said motor.

5. The dental handpiece of claim 1 wherein said motor casing has a notch, wherein said fastening means has a projection, said projection engaging said notch to provide connection between the motor casing and the fastening means.

6. A dental handpiece including, a handpiece section having a dental tool, and a driving section detachably connected at its distal end to the handpiece section, said driving section comprising:

a motor casing having a motor cavity extending from an open proximal end of said motor casing;

a motor slidably received within said motor cavity and restrained against rotation relative to said motor casing, said motor being slidably removable through said open proximal end; and, a cap detachably coupled to said proximal end of said motor casing for releasably fastening said motor in position in said motor cavity, said motor being slidably displaceable from said motor cavity subsequent to removal of said cap from said motor casing.

7. The dental handpiece of claim 6 wherein said motor casing has a notch at the proximal end, said cap having a projection, and said projection engaging said notch to provide connection between said motor casing and said cap.

8. The dental handpiece of claim 6 wherein said cap has a wave washer urging said motor distally in said motor cavity.

9. The dental handpiece of claim 6 wherein said motor casing has an inner surface, wherein said driving section further comprises two anti-rotation bars extending axially along and attached to said motor, said inner surface of said motor casing having two axially extending grooves for receiving said two anti-rotation bars.

10. The dental handpiece of claim 6 wherein said motor casing has fluid pipes and an optical fiber cable.

11. The dental handpiece of claim 10 wherein said motor cavity has a larger diameter portion and a smaller diameter portion, said smaller diameter portion having a central axis displaced with respect to a central axis of said motor casing.

12. The dental handpiece of claim 11 wherein said motor has a motor connector attached at a proximal end of said motor, said motor connector having a central axis displaced with respect to a central axis of said motor, said motor being positioned in said smaller diameter portion of said motor cavity, and said motor connector being positioned in said larger diameter portion.

13. The dental handpiece of claim 12 wherein said motor connector has fluid pipes detachably connected to said fluid pipes of said motor casing, and lighting means for supplying light to said optical fiber.

14. The dental handpiece of claim 13 wherein said cap has an aperture formed therethrough, and wherein said handpiece further comprises a cable connector detachably connected to said motor connector through said aperture of said cap for respectively supplying fluids and electric power to said fluid pipes and said lighting means of said motor connector.

* * * * *